(12) United States Patent
Fenton et al.

(10) Patent No.: US 10,478,611 B2
(45) Date of Patent: Nov. 19, 2019

(54) SWITCH

(71) Applicant: Sky Medical Technology Ltd., Cheshire (GB)

(72) Inventors: Jonathan Fenton, Greenwich (GB); Ali Ersan, London (GB); Martin Gordon, Buckinghamshire (GB)

(73) Assignee: Sky Medical Technology Ltd., Cheshire (GB)

( * ) Notice: Subject to any disclaimer, the term of this patent is extended or adjusted under 35 U.S.C. 154(b) by 0 days.

(21) Appl. No.: 15/540,838

(22) PCT Filed: Jan. 7, 2016

(86) PCT No.: PCT/GB2016/050032
§ 371 (c)(1),
(2) Date: Jun. 29, 2017

(87) PCT Pub. No.: WO2016/110705
PCT Pub. Date: Jul. 14, 2016

(65) Prior Publication Data
US 2018/0001076 A1    Jan. 4, 2018

(30) Foreign Application Priority Data

Jan. 7, 2015    (GB) .................................. 1500163.9

(51) Int. Cl.
*A61N 1/04*         (2006.01)
*H01H 13/702*       (2006.01)
(Continued)

(52) U.S. Cl.
CPC ......... *A61N 1/0452* (2013.01); *A61N 1/0456* (2013.01); *A61N 1/0484* (2013.01);
(Continued)

(58) Field of Classification Search
CPC ................. H01H 13/86; H01H 13/702; H01H 2207/028; H01H 2221/002;
(Continued)

(56) References Cited

U.S. PATENT DOCUMENTS 4,070,821 A     1/1978  Somogyi
4,190,748 A  *  2/1980  Langford .................. B41J 5/12
                                                200/5 A
(Continued)

FOREIGN PATENT DOCUMENTS

DE     37 16 379 A1    11/1987
EP     2 757 566 A1     7/2014
(Continued)

OTHER PUBLICATIONS

International Search Report and Written Opinion dated Mar. 23, 2016 in connection with International Application No. PCT/GB2016/050032.

(Continued)

*Primary Examiner* — Edwin A. Leon
*Assistant Examiner* — Lheiren Mae A Caroc
(74) *Attorney, Agent, or Firm* — Wolf, Greenfield & Sacks, P.C.

(57) ABSTRACT

A neuromuscular stimulation device is described having a plastic casing housing a printed circuit board bearing control electronics, with the casing including an external integral flexible portion which is capable of being flexed into the interior of the casing so as to cause an electrically insulative substrate on which is carried an electrically conductive pathway to be pushed into contact with the PCB in order to complete an electrical circuit. Such a switch is relatively inexpensive to produce, as it has few moving parts, can be formed in a usual manufacturing process, and is robust.

13 Claims, 3 Drawing Sheets

(51) Int. Cl.
  *H01H 13/86* (2006.01)
  *A61N 1/36* (2006.01)
(52) U.S. Cl.
  CPC ....... *A61N 1/36014* (2013.01); *H01H 13/702*
    (2013.01); *H01H 13/86* (2013.01); *H01H*
    *2205/006* (2013.01); *H01H 2207/028*
    (2013.01); *H01H 2207/034* (2013.01); *H01H*
    *2209/046* (2013.01); *H01H 2211/026*
    (2013.01); *H01H 2221/002* (2013.01); *H01H*
    *2223/002* (2013.01); *H01H 2223/04* (2013.01);
    *H01H 2229/044* (2013.01)
(58) Field of Classification Search
  CPC ............ H01H 2205/006; A61N 1/0452; A61N
    1/0484; A61N 1/0456; A61N 1/36014
  USPC ...................... 200/512, 513, 516, 517, 302.2
  See application file for complete search history.

(56) References Cited

U.S. PATENT DOCUMENTS

| | | | | |
|---|---|---|---|---|
| 4,322,587 | A * | 3/1982 | Burns ................. | H01H 13/702 200/5 R |
| 4,323,740 | A * | 4/1982 | Balash ................ | H01H 13/702 200/5 A |
| 4,763,308 | A | 8/1988 | Morata | |
| 4,896,178 | A | 1/1990 | Ohmura et al. | |
| 5,752,087 | A | 5/1998 | Sangregory | |
| 6,355,316 | B1 | 3/2002 | Miller et al. | |
| 7,764,936 | B2 * | 7/2010 | Nakasono .......... | G07C 9/00944 200/302.2 |
| 8,188,388 | B2 * | 5/2012 | Shimizu ............... | H01H 25/041 200/517 |
| 2004/0026222 | A1 | 2/2004 | Adachi | |
| 2014/0014730 | A1 | 1/2014 | Ledevehat | |
| 2014/0097073 | A1 * | 4/2014 | Kikuchi ................ | H01H 13/14 200/512 |
| 2014/0316310 | A1 | 10/2014 | Ackermann et al. | |
| 2018/0026240 | A1 | 1/2018 | Fenton et al. | |

FOREIGN PATENT DOCUMENTS

| | | |
|---|---|---|
| GB | 2210699 A | 6/1989 |
| GB | 2487758 A | 8/2012 |
| JP | 2002257960 A | 9/2002 |
| JP | 3875716 B1 | 1/2007 |
| WO | WO 99/03186 A | 1/1999 |
| WO | WO 2010/070332 A1 | 6/2010 |

OTHER PUBLICATIONS

International Preliminary Report on Patentability dated Jul. 20, 2017 in connection with International Application No. PCT/GB2016/050032.
International Search Report and Written Opinion dated Apr. 18, 2016 in connection with International Application No. PCT/GB2016/050033.
International Preliminary Report on Patentability dated Jul. 20, 2017 in connection with International Application No. PCT/GB2016/050033.
GB Search Report dated Jun. 25, 2015 in connection with GB Application No. GB1500164.7.
GB Search Report dated Jul. 2, 2015 in connection with GB Application No. GB1500163.9.
U.S. Appl. No. 15/540,769, filed Jun. 29, 2017, Fenton et al.
PCT/GB2016/050032, Mar. 23, 2016, International Search Report and Written Opinion.
PCT/GB2016/050032, Jul. 20, 2017, International Preliminary Report on Patentability.
PCT/GB2016/050033, Apr. 18, 2016, International Search Report and Written Opinion.
PCT/GB2016/050033, Jul. 20, 2017, International Preliminary Report on Patentability.

* cited by examiner

SWITCH

RELATED APPLICATIONS

This application is a 371 U.S. National Stage of International Application No. PCT/GB2016/050032, filed Jan. 7, 2016, which claims priority to United Kingdom Application No. 1500163.9, filed on Jan. 7, 2015.

FIELD OF THE INVENTION

The present invention relates to a switch configuration for incorporation into an electronic device. Aspects of the invention relate to an electronic device including such a switch. In particular, the switch is useful in disposable medical devices, for example an electronic neurostimulator device.

BACKGROUND TO THE INVENTION

Low cost, disposable electronic devices are used in many fields, including the medical device field. The present applicants have previously described an electronic neurostimulator device, in international patent application WO2010/070332. The device described therein incorporates a control unit housing the necessary electronics to drive the device, and to allow a user to operate the device; these typically include a PCB and an electrical cell. A pair of electrodes driven by the control unit are printed onto a flexible electrically insulative substrate (such as BoPET [Biaxially-oriented polyethylene terephthalate], for example Mylar®) along with electrically conductive tracks leading to the control unit. The substrate is mounted onto a more robust elongate tongue made from, for example, a flexible plastics material.

Such devices incorporate electrical switches to activate or deactivate the device, or to allow a user to adjust the intensity or other characteristics of the electrical stimulation. Incorporating suitable switches and their attendant moving parts into a low cost unit can be problematic, particularly when the unit is intended to be sealed or disposable. It is among the objects of embodiments of the present invention to provide an alternative switch configuration.

SUMMARY OF THE INVENTION

According to a first aspect of the present invention, there is provided an electronic device comprising:
  a plastic casing defining an interior and exterior, the interior housing a printed circuit board having an electrical contact point, the casing incorporating an external integral flexible portion which is capable of being flexed into the interior of the casing;
  a flexible electrically insulative substrate on which is carried an electrically conductive pathway;
  wherein at least a portion of the flexible substrate is retained by the casing such that said portion is adjacent to but spaced from the PCB;
  such that when the integral flexible portion is flexed into the interior of the casing, it urges said portion of the flexible substrate into contact with the PCB, such that the electrically conductive pathway contacts the electrical contact point, thereby completing an electrical circuit.

This arrangement allows a switch to be formed from a substrate bearing a printed circuit in combination with a printed circuit board (PCB) bearing control electronics. The printed circuit on the substrate and the PCB are arranged with respect to one another such that the two are brought into contact on actuating the integral flexible portion of the casing, which completes an electrical circuit. This may be used to activate or deactivate a device, or to adjust operating parameters. The switch is relatively inexpensive to produce, as it has few moving parts, and can be formed in the usual manufacturing process, and is robust.

In a preferred embodiment, the external integral flexible portion is resilient, such that when force is applied to the integral flexible portion it is flexed into the interior of the casing, and when force is not applied, it is no longer so flexed. This allows the flexible portion to act as a spring, and to reopen the switch after closure. There is thus no need to include an additional spring to reopen the switch.

Preferably the external integral flexible portion is formed in a dome shape. This feature also gives tactile feedback when pressed. This occurs when the dome is deformed during activation. Both the overall form of the dome and the properties of the polymer help the button/dome to restructure into its original state.

Preferably the portion of the flexible substrate is retained by the casing under tension. For example, the flexible substrate may be disposed within a tortuous path formed within the casing, such that the substrate is retained by the casing. Keeping the substrate under tension also allows the substrate to act somewhat as a spring, as well as retaining it fast within the casing to prevent or reduce unwanted movement. The casing may be formed from two portions which are secured together (for example, by welding, such as ultrasonic welding), and the tortuous path is formed between the two portions.

The flexible substrate may extend beyond the casing. This allows electrical signals to be taken outside the casing; for example, to drive electrodes mounted beyond the casing for use as neuromuscular stimulation devices.

The flexible substrate may be a polymeric substrate, preferably a biaxially-oriented polyethylene terephthalate film, for example Mylar®.

The integral flexible portion may comprise an internal protrusion, sized and shaped to assist in urging the flexible substrate into contact with the PCB: for example, a pin or pins extending from an inner surface of the flexible portion on the casing.

The device may further comprise an electrical cell within the casing.

The device may comprise a plurality of external integral flexible portions, and a corresponding plurality of electrical contact points on the PCB—that is, the device includes multiple switches.

Preferably the casing is substantially sealed against moisture ingress.

Preferably the casing is injection moulded.

The device is preferably a medical device, for example an electrical neuromuscular stimulator. However, the switch may be incorporated into any number of devices, as will be readily apparent to the skilled person.

Also provided by the present invention is an electrical switch comprising:
  a plastic casing defining an interior and exterior, the interior housing a printed circuit board having an electrical contact point, the casing incorporating an external integral flexible portion which is capable of being flexed into the interior of the casing;
  a flexible electrically insulative substrate on which is carried an electrically conductive pathway;

wherein at least a portion of the flexible substrate is retained by the casing such that said portion is adjacent to but spaced from the PCB;

such that when the integral flexible portion is flexed into the interior of the casing, it urges said portion of the flexible substrate into contact with the PCB, such that the electrically conductive pathway contacts the electrical contact point, thereby completing an electrical circuit.

DETAILED DESCRIPTION OF THE INVENTION

Figure 1:
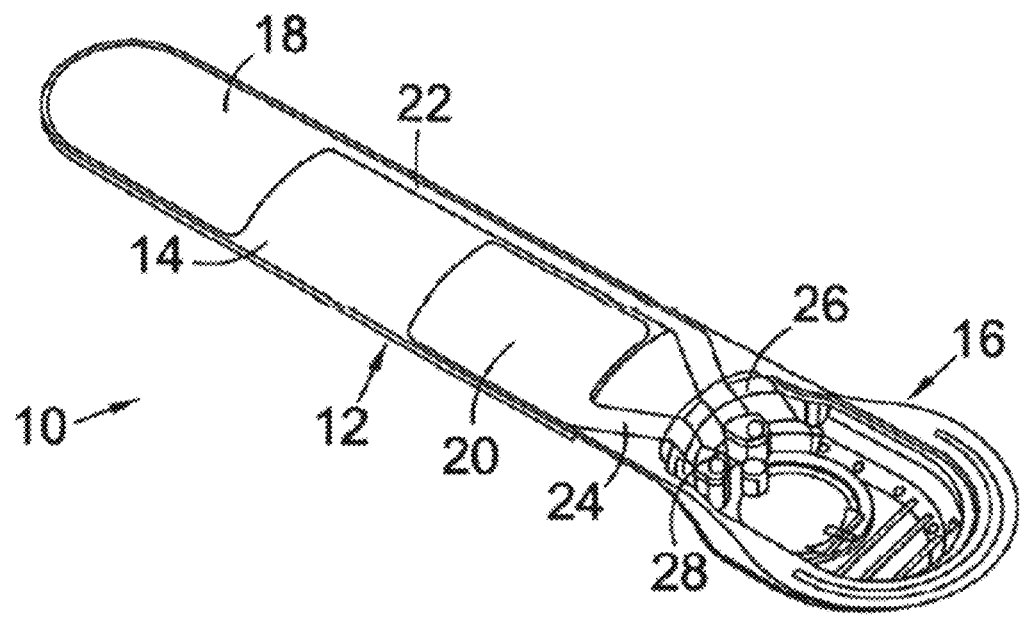
FIG. 1 shows an electronic neuromuscular stimulation device, taken from WO2010/070332.

Shown in FIG. 1 is a neuromuscular stimulator device 10 as described in WO2010/070332. The device comprises a flexible, non-stretchable thermoplastic elastomer substrate 12 which includes an elongate tongue 14 at one end, and a moulded recess 16 at the other.

On the tongue 14 are printed positive 18 and negative 20 electrodes. The positive is slightly larger than the negative. Each electrode includes a conductive track 22, 24 leading from the electrode to a respective contact point 26, 28 located in the recess 16. Not shown in the figures are an insulative strip arranged between the positive track 22 and the negative electrode 20, and similar strips at the edges of the tongue, to prevent unwanted leakage of current.

Within the recess 16 are placed an electrical cell (not shown), and a PCB (not shown) including suitable circuitry to control the electrodes. Together with the conductive tracks 22, 24 and contact points 26, 28, this forms a complete circuit. A plastic cover is then sonically welded over the recess 16 to seal the components. A layer of gel is then placed over the whole device 10; this provides an electrical contact with a user's limb and helps keep the device adhered to a user. The gel may be protected in transit by a peelable backing layer.

The outer surface of the recess 16 is formed with an integral diaphragm button 30 and an aperture 32 for displaying an LED. The button 30 is arranged to contact a corresponding button on the battery housing or PCB to activate the device. The aperture 32 displays an LED which indicates whether the device is operating.

In order to incorporate the switch arrangement as described herein, the device 10 is modified in a number of ways. The positive 18 and negative 20 electrodes are printed on a BoPET (eg, Mylar®) flexible substrate, which is itself affixed to the elongate tongue 14. The substrate also carries conductive tracks for connecting the electrodes to the control circuitry on the PCB. Further, the button 30 does not itself contact a corresponding button on the battery housing or PCB, as will be described.

Figure 5:
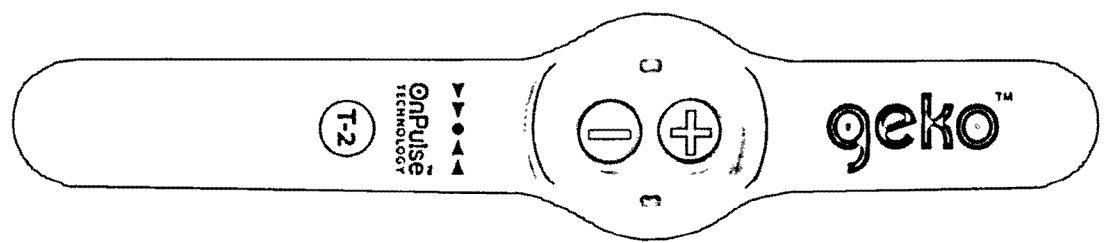
FIGS. 5 and 6 show an alternative device.
Figure 6:
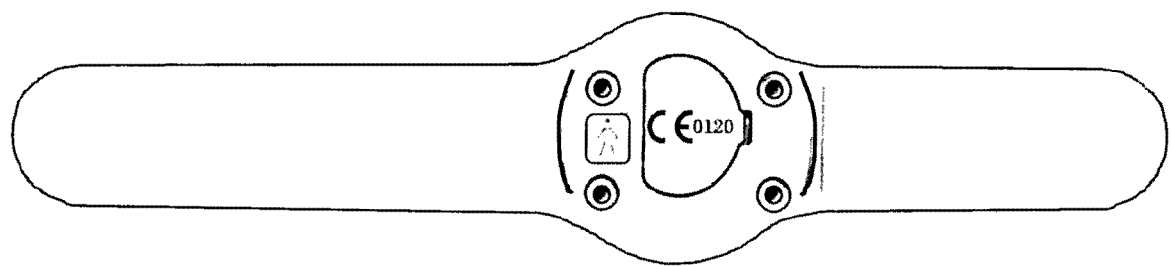

An alternative device is shown in external view in FIGS. 5 and 6. This is generally similar in operation to the device shown in FIG. 1, but has a slightly different configuration, in that the recess/enclosure is located towards the centre of the flexible tongue. The presence of two dome-shaped push buttons can be seen on the upper surface of the device, in FIG. 5. A view of the device from the lower surface is shown in FIG. 6.

Figure 2:
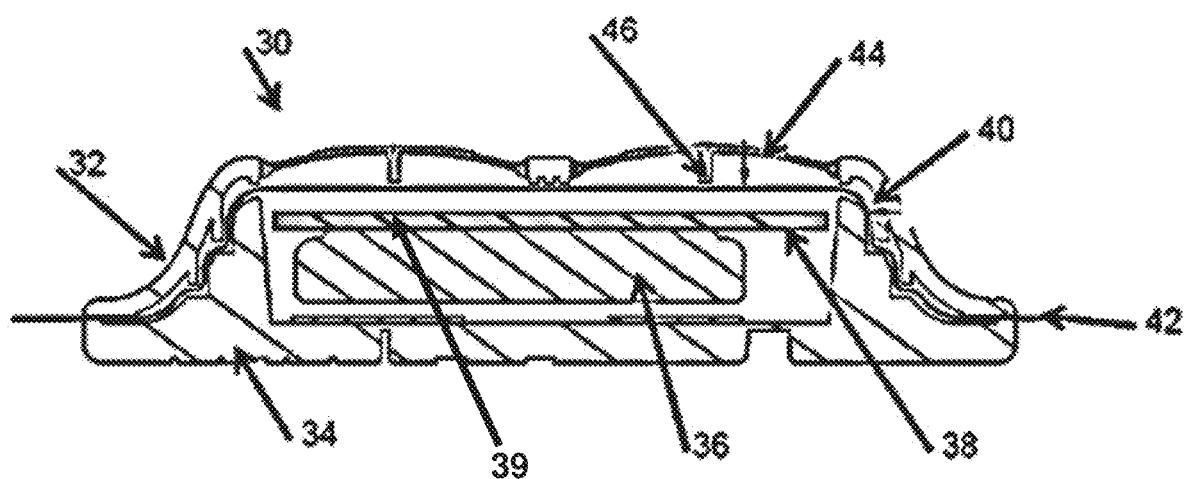
FIG. 2 shows a section of the control module of a device, incorporating a switch arrangement in accordance with an embodiment of the present invention.

FIG. 2 shows a section of the modified device of FIGS. 5 and 6, in accordance with an embodiment of the invention. The figure shows a housing 30 forming an enclosure (corresponding to the recess 16 of FIG. 1). The housing 30 is formed of two injection moulded plastic parts (32, 34), forming upper and lower portions of the housing. The elongate tongue 14 can be connected to flanges formed at either end of the housing 30. Within the housing 30 are located an electrical cell 36 and a PCB 38. The two portions of the housing are welded together to form a watertight seal; for example, by ultrasonic welding.

The housing 30 includes a tortuous path 40 formed therein between the upper and lower portions 32, 34, with the path being formed as a gap between the portions. Within this path 40 is placed the Mylar flexible substrate 42, which extends beyond the housing where it may be fixed to the tongue 14. On the lower surface (as seen in the figure) of the substrate 42 are printed a pair of electrodes and electrically conductive tracks for connecting the substrate to the PCB 30 and cell 36. The tortuous path 40 serves to retain the substrate 42 under tension, such that it is suspended above the PCB 38, and such that it does not move with respect to the housing.

On the upper external surface of the upper portion 32 of the housing 30 are formed a pair of switches in the form of flexible protruding domes 44; each dome 44 includes an inwardly extending pin 46. The domes 44 and pins 46 are integrally formed within the housing. The domes 44 in particular are formed of a resilient material, such that they deform under pressure, but return to their original position upon removal of that pressure. In some embodiments of the invention, the domes may merely be formed of a deformable material, such that they do not revert to their original position.

Figure 3:
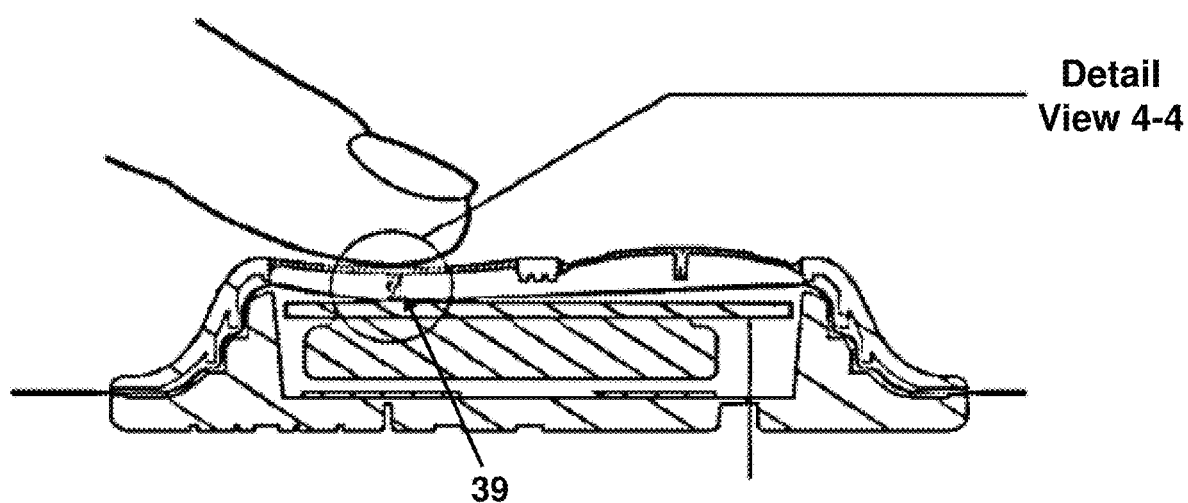
FIG. 3 shows the control module of FIG. 2, when being activated by a user.
Figure 4:
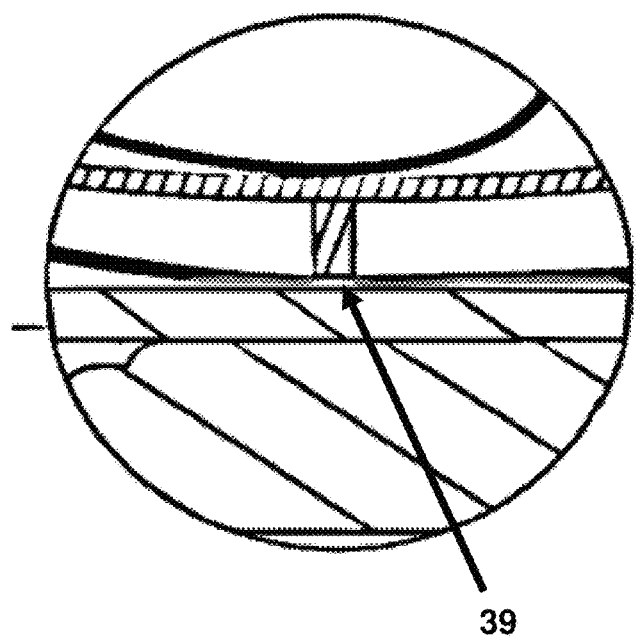
FIG. 4 shows an enlarged view of the portion of FIG. 3 labeled "Detail View 4-4".

In order to actuate the switches, a user will exert pressure on the domes 44 (shown in FIGS. 3 and 4) with their finger. The dome 44 deforms and extends inwardly into the housing 30; this in turn urges the pin 46 into contact with the substrate 42 which is thus pressed into contact with the electrical contact point 39 of PCB 38. A portion of the conductive track printed on the substrate 42 thus contacts a conductive portion formed on the PCB, thereby forming a complete electrical circuit and closing the switch. When the user releases the switch, the resilience of the plastics material will allow the dome 44 to revert to the original position, while the tension in the substrate 42 also assists by acting as a spring. This separates the substrate 42 from the PCB 38, thereby opening the switch. The dome shape of the switch, in combination with the resilient nature of the substrate and the presence of the pin will together provide tactile feedback to the user.

In certain embodiments, the domes 44 may not be resilient, such that the switch will remain closed, this might be of use for a single-use button or circuit.

Although the switch has been described in the context of a medical device for neuromuscular stimulation, it will be apparent that its applicability is not so limited. In particular, the switch arrangement it ideally suited for low cost, disposable applications, in that there are relatively few moving parts, and the switch can be formed out of those components (casing, substrate, PCB) which will be used in an electronic device anyway. Further, the casing may be sealed to result in a largely waterproof device. The present inventors particularly envisage the switch as being of benefit in mobile telephones, watches, control panels, or keyboards, among others.

The invention claimed is:

1. An electronic device comprising:
   a plastic casing defining an interior and exterior, the interior housing a printed circuit board having an electrical contact point, the casing incorporating an external integral flexible portion which is capable of being flexed into the interior of the casing;
   a flexible electrically insulative substrate on which is carried an electrically conductive pathway;
   a pair of electrodes that provide neuromuscular stimulation, located on the flexible electrically insulative substrate, the flexible electrically insulative substrate and the electrically conductive pathway extending out of the interior of the casing to the exterior of the casing to drive the electrodes, the electrodes being located outside the casing;
   wherein at least a portion of the flexible electrically insulative substrate is retained by the casing such that said portion is adjacent to but spaced from the printed circuit board;
   such that when the integral flexible portion is flexed into the interior of the casing, the integral flexible portion urges said portion of the flexible electrically insulative substrate into contact with the printed circuit board, such that the electrically conductive pathway contacts the electrical contact point, thereby completing an electrical circuit.

2. The device of claim 1, wherein the external integral flexible portion is resilient, such that when force is applied to the integral flexible portion, the integral flexible portion is flexed into the interior of the casing, and when force is not applied, the integral flexible portion is no longer so flexed.

3. The device of claim 1, wherein the external integral flexible portion is formed in a dome shape.

4. The device of claim 1, wherein the portion of the flexible electrically insulative substrate is retained by the casing under tension.

5. The device of claim 1, wherein the flexible electrically insulative substrate is disposed within a tortuous path formed within the casing, such that the substrate is retained by the casing.

6. The device of claim 5, wherein the casing is formed from two portions which are secured together, and the tortuous path is formed between the two portions.

7. The device of claim 1, wherein the flexible electrically insulative substrate is a polymeric substrate.

8. The device of claim 7, wherein the flexible electrically insulative substrate is a biaxially-oriented polyethylene terephthalate film.

9. The device of claim 1, wherein the integral flexible portion comprises an internal protrusion, sized and shaped to assist in urging the flexible electrically insulative substrate into contact with the printed circuit board.

10. The device of claim 1, wherein the casing further comprises an electrical cell.

11. The device of claim 1, comprising a plurality of external integral flexible portions, and a corresponding plurality of electrical contact points on the printed circuit board.

12. The device of claim 1, wherein the casing is substantially sealed against moisture ingress.

13. The device of claim 1, wherein the casing is injection moulded.

* * * * *